US009657096B2

(12) United States Patent
Dimitrov et al.

(10) Patent No.: US 9,657,096 B2
(45) Date of Patent: May 23, 2017

(54) HUMAN DOMAIN ANTIBODIES AGAINST COMPONENTS OF THE HUMAN INSULIN-LIKE GROWTH FACTOR (IGF) SYSTEM

(71) Applicant: The United States of America, as represented by the Secretary, Department of Health and Human Services, Washington, DC (US)

(72) Inventors: Dimiter S. Dimitrov, Frederick, MD (US); Weizao Chen, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/710,875

(22) Filed: May 13, 2015

(65) Prior Publication Data
US 2015/0246967 A1   Sep. 3, 2015

Related U.S. Application Data

(62) Division of application No. 13/499,758, filed as application No. PCT/US2010/051784 on Oct. 7, 2010, now Pat. No. 9,056,907.

(60) Provisional application No. 61/249,476, filed on Oct. 7, 2009.

(51) Int. Cl.
| | |
|---|---|
| *G01N 33/53* | (2006.01) |
| *A61K 39/395* | (2006.01) |
| *C07K 16/28* | (2006.01) |
| *A61K 39/00* | (2006.01) |
| *C07K 16/22* | (2006.01) |
| *G01N 33/74* | (2006.01) |

(52) U.S. Cl.
CPC ........ *C07K 16/22* (2013.01); *A61K 39/39591* (2013.01); *C07K 16/2863* (2013.01); *G01N 33/74* (2013.01); *A61K 2039/505* (2013.01); *C07K 2317/21* (2013.01); *C07K 2317/33* (2013.01); *C07K 2317/565* (2013.01); *C07K 2317/569* (2013.01); *C07K 2317/73* (2013.01); *C07K 2317/76* (2013.01); *C07K 2317/92* (2013.01); *C07K 2319/00* (2013.01); *G01N 2333/71* (2013.01)

(58) Field of Classification Search
None
See application file for complete search history.

(56) References Cited

U.S. PATENT DOCUMENTS

| | | |
|---|---|---|
| 2006/0165695 A1 | 7/2006 | Shitara et al. |
| 2006/0240015 A1 | 10/2006 | Shitara et al. |
| 2008/0014203 A1 | 1/2008 | Hansen et al. |
| 2008/0025990 A1 | 1/2008 | Ludwig |
| 2008/0226635 A1 | 9/2008 | Koll et al. |

FOREIGN PATENT DOCUMENTS

| | | |
|---|---|---|
| WO | WO 2008/155387 | 12/2008 |
| WO | WO 2011/044336 | * 4/2011 |

OTHER PUBLICATIONS

Burtrum et al., A Fully Human Monoclonal Antibody to the Insulin-Like Growth Factor I Receptor Blocks Ligand-Dependent Signaling and Inhibits Human Tumor Growth in Vivo, *Cancer Res.*, vol. 63:8912-8921, 2003.
Chen et al., "Construction of a Large Phage-Displayed Human Antibody Domain Library with a Scaffold Based on a Newly Identified Highly Soluble, Stable Heavy Chain Variable Domain," *J. Mol. Biol.*, vol. 382:779-789, 2008.
De Bernardis et al., "Human Domain Antibodies against Virulence Traits of Candida albicans Inhibit Fungus Adherence to Vaginal Epithelium and protect against Experimental Vaginal Candidiasis," *J Infect Dis* 195:149-157, 2007.
Feng et al., "Novel Human Monoclonal Antibodies to Insulin-Like Growth Factor (IGF)-II that Potently Inhibit the IGF Receptor Type I Signal Transduction Function," *Mol. Cancer Ther.*, vol. 5(1):114-120, 2006.
Hailey et al., "Neutralizing Anti-Insulin-like Growth Factor Receptor 1 Antibodies Inhibit Receptor Function and Induce Receptor Degradation in Tumor Cells," *Mol. Cancer Ther.*, vol. 1:1349-1353, 2002.
Holt et al., Domain Antibodies: Proteins for Therapy, vol. 21(11):484-490, 2003.
LeRoith et al., "The Insulin-Like Growth Factor System and Cancer," *Cancer Letters*, vol. 195:127-137, 2003.
Sachdev et al., "Down-regulation of Insulin Receptor by Antibodies against the Type I Insulin-Like Growth Factor Receptor: Implications for Anti-Insulin-Like Growth Factor Therapy in Breast Cancer," *Cancer Res.*, vol. 66:2391-2402, 2006.
Wesolowski et al., "Single domain antibodies: promising experimental and therapeutic tools in infection and immunity," *Med Microbiol Immunol* 198:157-174, 2009.

* cited by examiner

*Primary Examiner* — Marianne P Allen
(74) *Attorney, Agent, or Firm* — Klarquist Sparkman, LLP

(57) ABSTRACT

Antibodies and antibody fragments that bind to insulin-like growth factor (IGF) 1 receptor (IGF-1R) or IGF-2, as well as methods of using the antibodies for inhibiting the IGF-mediated signaling pathway, inhibiting IGF-1R signaling, and treating cancer, are described. A method of detecting the presence of IGF-1R or IGF-2 in a sample using the disclosed antibodies and antibody fragments is also described.

8 Claims, No Drawings

SEQUENCE LISTING

```
<160> NUMBER OF SEQ ID NOS: 28

<210> SEQ ID NO 1
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 1

Gln Gln Tyr Lys Thr Tyr Pro Leu Thr Phe
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 2

Ile Ser Gly Ser Gly Gly Thr Thr
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 3

Ala Arg Val Ala Ser Arg Asp Tyr Phe Asp Tyr
1               5                   10

<210> SEQ ID NO 4
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 4

Gln Val Gln Leu Val Gln Ser Gly Gly Gly Leu Val Gln Pro Gly Gly
1               5                   10                  15

Ser Leu Arg Leu Ser Cys Ala Ala Ser Asp Tyr Ser Gln Gln Tyr Lys
                20                  25                  30

Thr Tyr Pro Leu Thr Phe Met Ser Trp Val Arg Gln Ala Pro Gly Gln
            35                  40                  45

Arg Leu Glu Trp Val Ala Gly Ile Ser Gly Ser Gly Gly Thr Thr Val
        50                  55                  60
```

```
Tyr Ala Asp Ser Val Lys Gly Arg Phe Thr Ile Ser Arg Asp Asn Ser
 65                  70                  75                  80

Lys Asn Thr Leu Tyr Leu Gln Met Asn Thr Leu Arg Ala Glu Asp Thr
                 85                  90                  95

Ala Met Tyr Tyr Cys Ala Arg Val Ala Ser Arg Asp Tyr Phe Asp Tyr
            100                 105                 110

Trp Gly Gln Gly Thr Leu Val Thr Val Ser Ser
            115                 120

<210> SEQ ID NO 5
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 5

Leu Gln His Asp Asn Phe Pro Tyr Thr Phe
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 6

Ile Ser Gly Ser Gly Gly Ser Thr
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 7

Ala Arg Ile Arg Trp Leu Gln Asp Leu Asp Tyr
1               5                   10

<210> SEQ ID NO 8
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 8

Gln Val Gln Leu Val Gln Ser Gly Gly Gly Leu Val Gln Pro Gly Gly
1               5                   10                  15

Ser Leu Arg Leu Ser Cys Ala Ala Ser Tyr Tyr Ser Leu Gln His Asp
                20                  25                  30

Asn Phe Pro Tyr Thr Phe Met Ser Trp Val Arg Gln Ala Pro Gly Gln
            35                  40                  45

Arg Leu Glu Trp Val Ser Gly Ile Ser Gly Ser Gly Gly Ser Thr Tyr
        50                  55                  60

Tyr Ala Asp Ser Val Lys Gly Arg Phe Thr Ile Ser Arg Asp Asn Ser
 65                  70                  75                  80

Lys Asn Thr Leu Tyr Leu Gln Met Asn Thr Leu Arg Ala Glu Asp Thr
                 85                  90                  95
```

Ala Met Tyr Tyr Cys Ala Arg Ile Arg Trp Leu Gln Asp Leu Asp Tyr
                100                 105                 110

Trp Gly Gln Gly Thr Leu Val Thr Val Ser Ser
        115                 120

<210> SEQ ID NO 9
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 9

Gln Gln Tyr Asn Ser Tyr Pro Ile Thr Phe
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 10

Ile Asn Gln Asp Gly Ser Gln Ile
1               5

<210> SEQ ID NO 11
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 11

Ala Val Asp Leu Arg Ser Gly Ala Arg Asn Phe Gln His
1               5                   10

<210> SEQ ID NO 12
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 12

Gln Val Gln Leu Val Gln Ser Gly Gly Gly Leu Val Gln Pro Gly Gly
1               5                   10                  15

Ser Leu Arg Leu Ser Cys Ala Ala Ser Tyr Tyr Ser Gln Gln Tyr Asn
            20                  25                  30

Ser Tyr Pro Ile Thr Phe Met Ser Trp Val Arg Gln Ala Pro Gly Gln
        35                  40                  45

Arg Leu Glu Trp Val Ala Ser Ile Asn Gln Asp Gly Ser Gln Ile Asp
    50                  55                  60

Tyr Ala Gly Ser Val Lys Gly Arg Phe Thr Ile Ser Arg Asp Asn Ser
65                  70                  75                  80

Lys Asn Thr Leu Tyr Leu Gln Met Asn Thr Leu Arg Ala Glu Asp Thr
                85                  90                  95

Ala Thr Tyr Tyr Cys Ala Val Asp Leu Arg Ser Gly Ala Arg Asn Phe
            100                 105                 110

Gln His Trp Gly Gln Gly Thr Leu Val Thr Val Ser Ser
        115                 120                 125

```
<210> SEQ ID NO 13
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 13

Asp Phe Tyr Phe Tyr Asp Tyr Glu
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 14

Ile Ser His Gly Gly Ile Thr
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 15

Ala Arg Asp Tyr Gly Tyr Ala Phe Asp Ile
1               5                   10

<210> SEQ ID NO 16
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 16

Gln Val Gln Leu Val Gln Ser Gly Gly Gly Leu Val Gln Pro Gly Gly
1               5                   10                  15

Ser Leu Arg Leu Ser Cys Ala Ala Ser Asp Phe Tyr Phe Tyr Asp Tyr
            20                  25                  30

Glu Met Ser Trp Val Arg Gln Ala Pro Gly Lys Gly Leu Glu Trp Ile
        35                  40                  45

Gly Ser Ile Ser His Gly Gly Ile Thr His Tyr Thr Tyr Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Met Tyr Tyr Cys Ala
                85                  90                  95

Arg Asp Tyr Gly Tyr Ala Phe Asp Ile Trp Gly Gln Thr Thr Gly
            100                 105                 110

Thr Val Ser Ser
        115

<210> SEQ ID NO 17
<211> LENGTH: 8
<212> TYPE: PRT
<213> ORGANISM: Artificial Sequence
<220> FEATURE:
<223> OTHER INFORMATION: Synthetic polypeptide
```

```
<400> SEQUENCE: 17

Ser Phe Ser Phe Ser Asp Tyr Glu
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 18

Ile Asn Ser Asp Gly Val Ile
1               5

<210> SEQ ID NO 19
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 19

Val Arg Val Ala Val Pro Gly Lys Arg Tyr Phe Gln Tyr
1               5                   10

<210> SEQ ID NO 20
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 20

Gln Val Gln Leu Val Gln Ser Gly Gly Gly Leu Val Gln Pro Gly Gly
1               5                   10                  15

Ser Leu Arg Leu Ser Cys Ala Ala Ser Ser Phe Ser Phe Ser Asp Tyr
            20                  25                  30

Glu Met Ser Trp Val Arg Gln Ala Pro Gly Lys Gly Leu Glu Trp Val
        35                  40                  45

Ala His Ile Asn Ser Asp Gly Val Ile Gln Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Thr Leu Arg Ala Glu Asp Thr Ala Thr Tyr Tyr Cys Val
                85                  90                  95

Arg Val Ala Val Pro Gly Lys Arg Tyr Phe Gln Tyr Trp Gly Gln Gly
            100                 105                 110

Thr Thr Val Thr Val Ser Ser
        115

<210> SEQ ID NO 21
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 21

Gln Ser Phe Asp Ser Asp Ser Val Val Phe
1               5                   10
```

```
<210> SEQ ID NO 22
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 22

Met Ser Asn Thr Gly Thr Tyr Ile
1               5

<210> SEQ ID NO 23
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 23

Val Lys Glu Trp Asp Arg Gly Leu Arg Arg Leu Gln His
1               5                   10

<210> SEQ ID NO 24
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 24

Gln Val Gln Leu Val Gln Ser Gly Gly Gly Leu Val Gln Pro Gly Gly
1               5                   10                  15

Ser Leu Arg Leu Ser Cys Ala Ala Ser Tyr Tyr Gly Gln Ser Phe Asp
                20                  25                  30

Ser Asp Ser Val Val Phe Met Ser Trp Val Arg Gln Ala Pro Gly Lys
            35                  40                  45

Gly Leu Glu Trp Ile Ser Ser Met Ser Asn Thr Gly Thr Tyr Ile Asp
        50                  55                  60

Tyr Ala Asp Ser Val Lys Gly Arg Phe Thr Ile Ser Arg Asp Asn Ser
65                  70                  75                  80

Lys Asn Thr Leu Tyr Leu Gln Met Asn Thr Leu Arg Ala Glu Asp Thr
                85                  90                  95

Ala Thr Tyr Tyr Cys Val Lys Glu Trp Asp Arg Gly Leu Arg Arg Leu
            100                 105                 110

Gln His Trp Gly Gln Gly Thr Val Val Thr Val Ser Ser
        115                 120                 125

<210> SEQ ID NO 25
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 25

Gln Gln Thr Tyr Ser Ala Pro Ile Thr Phe
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Synthetic polypeptide
```

```
<400> SEQUENCE: 26

Thr Ser Trp Asn Gly Gly Thr Thr
1               5

<210> SEQ ID NO 27
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 27

Val Thr Asp Thr Ser Gly Trp Arg Tyr Phe Gln Asp
1               5                   10

<210> SEQ ID NO 28
<211> LENGTH: 124
<212> TYPE: PRT
<213> ORGANISM: Artificial Sequence
<220> FEATURE:
<223> OTHER INFORMATION: Synthetic polypeptide

<400> SEQUENCE: 28

Gln Val Gln Leu Val Gln Ser Gly Gly Gly Leu Val Gln Pro Gly Gly
1               5                   10                  15

Ser Leu Arg Leu Ser Cys Ala Ala Ser Asn Tyr Ser Gln Gln Thr Tyr
            20                  25                  30

Ser Ala Pro Ile Thr Phe Met Ser Trp Val Arg Gln Ala Pro Gly Gln
        35                  40                  45

Gly Leu Glu Trp Val Ser Ser Thr Ser Trp Asn Gly Gly Thr Thr Asp
    50                  55                  60

Tyr Ala Asp Ser Val Lys Gly Arg Phe Thr Ile Ser Arg Asp Asn Ser
65                  70                  75                  80

Lys Asn Thr Leu Tyr Leu Gln Met Asn Thr Leu Arg Ala Glu Asp Thr
                85                  90                  95

Ala Met Tyr Tyr Cys Val Thr Asp Thr Ser Gly Trp Arg Tyr Phe Gln
            100                 105                 110

Asp Trp Gly Gln Gly Thr Leu Val Thr Val Ser Ser
            115                 120
```

HUMAN DOMAIN ANTIBODIES AGAINST COMPONENTS OF THE HUMAN INSULIN-LIKE GROWTH FACTOR (IGF) SYSTEM

CROSS REFERENCE TO RELATED APPLICATIONS

This is a divisional of U.S. application Ser. No. 13/499,758, filed Apr. 2, 2012, issued as U.S. Pat. No. 9,056,907 on Jun. 16, 2015, which is the U.S. National Stage of International Application No. PCT/US2010/051784, filed Oct. 7, 2010, published in English under PCT Article 21(2), which claims the benefit of U.S. Provisional Application No. 61/249,476, filed Oct. 7, 2009. The above-referenced applications are herein incorporated by reference in their entirety.

SEQUENCE LISTING

The Sequence Listing is submitted as an ASCII text file, created on Apr. 30, 2015, 12.4 KB, which is incorporated by reference herein.

BACKGROUND

Insulin-like growth factor (IGF) 1 receptor (IGF-1R) is a receptor tyrosine kinase that is widely expressed in human epithelial cancers (see, e.g., LeRoith et al., Cancer Letters, 195: 127-137 (2003)). The receptor is activated by its cognate ligands, insulin-like growth factor 1 (IGF-1) and 2 (IGF-2). IGF binding activates intrinsic tyrosine kinase activity, resulting in receptor autophosphorylation and stimulation of signaling cascades that include the IRS-1/PI-3K/AKT/mTOR, and Grb2/Sos/Ras/MAPK pathways. The IGF mediated signaling has been implicated in the development of several epithelial cancers, such prostate, breast, and colorectal cancers. There is a need for cancer therapeutic agents that target the IGF mediated signaling pathway.

SUMMARY

The invention provides a single domain antibody comprising (a) SEQ ID NO: 1, SEQ ID NO: 2, and SEQ ID NO: 3; (b) SEQ ID NO: 5, SEQ ID NO: 6, and SEQ ID NO: 7; (c) SEQ ID NO: 9, SEQ ID NO: 10, and SEQ ID NO: 11; (d) SEQ ID NO: 13, SEQ ID NO: 14, and SEQ ID NO: 15; (e) SEQ ID NO: 17, SEQ ID NO: 18, and SEQ ID NO: 19; (f) SEQ ID NO: 21, SEQ ID NO: 22, and SEQ ID NO: 23; or (g) SEQ ID NO: 25, SEQ ID NO: 26, and SEQ ID NO: 27, as well as a nucleic acid encoding the antibody and cell comprising the nucleic acid.

The invention also provides a method of inhibiting insulin-like growth factor (IGF) mediated signaling pathway in a mammal comprising administering to the mammal a single domain antibody comprising (a) SEQ ID NO: 1, SEQ ID NO: 2, and SEQ ID NO: 3; (b) SEQ ID NO: 5, SEQ ID NO: 6, and SEQ ID NO: 7; or (c) SEQ ID NO: 9, SEQ ID NO: 10, and SEQ ID NO: 11, or a fusion protein or conjugate comprising the antibody, or a nucleic encoding the antibody, whereby the IGF mediated signaling pathway is inhibited.

The invention additionally provides a method of treating a cancer associated with the expression of IGF in a mammal comprising administering to the mammal a single domain antibody comprising (a) SEQ ID NO: 1, SEQ ID NO: 2, and SEQ ID NO: 3; (b) SEQ ID NO: 5, SEQ ID NO: 6, and SEQ ID NO: 7; or (c) SEQ ID NO: 9, SEQ ID NO: 10, and SEQ ID NO: 11, or a fusion protein or conjugate comprising the antibody, or a nucleic encoding the antibody, whereby the cancer is treated.

The invention further provides a method of detecting the presence of IGF-2 or IGF-1R in a sample comprising contacting the sample with a single domain antibody comprising (a) SEQ ID NO: 13, SEQ ID NO: 14, and SEQ ID NO: 15; (b) SEQ ID NO: 17, SEQ ID NO: 18, and SEQ ID NO: 19; (c) SEQ ID NO: 21, SEQ ID NO: 22, and SEQ ID NO: 23; or (d) SEQ ID NO: 25, SEQ ID NO: 26, and SEQ ID NO: 27, wherein binding of the single domain antibody to IGF-2 or IGF-1R indicates the presence of IGF-2 or IGF-1R in the sample.

Also provided herein are related compositions, kits, and methods, such as methods for preparing dAbs.

DETAILED DESCRIPTION

Provided herein is a single domain antibody (dAb), which is also known as an engineered antibody domain (eAd), that binds to human insulin growth factor 1 receptor (IGF-1R) or IGF ligand 2 (IGF-2). Single domain antibodies comprise only a single variable domain, such as the heavy-chain variable region ($V_H$) or light-chain variable region ($V_L$) (Ward et al., Nature, 341: 544-546 (1989); Holt et al., TRENDS in Biotechnology, 21(11): 484-490 (2003)). The variable region, in turn, comprises complimentary determining regions (CDRs) that confer binding specificity, and framework regions, which those parts of the variable domain other than the CDRs. dAbs are highly expressed in microbial cell culture, show favorable biophysical properties including solubility and temperature stability, and are well suited to selection and affinity maturation by in vitro selection systems such as phage display. dAbs also are bioactive as monomers and, owing to their small size and inherent stability, can be formatted into larger molecules to create drugs with prolonged serum half-lives or other pharmacological activities.

The dAb can have any suitable framework region. However, in a preferred embodiment, the single domain antibody is human or humanized to lessen the chance that an antibody administered to a human will evoke an undesirable immune response. Thus, the framework region of the dAb, desirably, is that of a human variable domain. Most preferably, the antibody comprises the framework regions derived from a human heavy-chain variable domain. However, in some instances, one or more framework (FR) residues of the human antibody can be replaced by corresponding non-human residues, such as FR residues from analogous sites in rodent antibodies (Jones et al., Nature, 321:522-525 (1986), Reichmann et al., Nature, 332:323-327 (1988); Presta, Curr. Opin. Struct. Biol., 2:593-596 (1992)).

The antibody provided herein comprises three CDRs. In a first embodiment, the antibody comprises as the CDRs SEQ ID NO: 1, SEQ ID NO: 2, and SEQ ID NO: 3. One example of such a single domain antibody, wherein the framework region is that of a human heavy chain variable domain, is a single domain antibody comprising SEQ ID NO: 4 (m632).

In a second embodiment, the single domain antibody comprises as the CDRs SEQ ID NO: 5, SEQ ID NO: 6, and SEQ ID NO: 7. One example of such a single domain antibody, wherein the framework region is that of a human heavy chain variable domain, is a single domain antibody comprising SEQ ID NO: 8 (m636).

In a third embodiment, the single domain antibody comprises as the CDRs SEQ ID NO: 9, SEQ ID NO: 10, and SEQ ID NO: 11. One example of such a single domain antibody, wherein the framework region is that of a human heavy chain variable domain, is a single domain antibody comprising SEQ ID NO: 12 (m546).

In a fourth embodiment, the single domain antibody comprises as the CDRs SEQ ID NO: 13, SEQ ID NO: 14, and SEQ ID NO: 15. One example of such a single domain antibody, wherein the framework region is that of a human heavy chain variable domain, is a single domain antibody comprising SEQ ID NO: 16 (m534).

In a fifth embodiment, the single domain antibody comprises as the CDRs SEQ ID NO: 17, SEQ ID NO: 18, and SEQ ID NO: 19. One example of such a single domain antibody, wherein the framework region is that of a human heavy chain variable domain, is a single domain antibody comprising SEQ ID NO: 20 (m535).

In a sixth embodiment, the single domain antibody comprises as the CDRs SEQ ID NO: 21, SEQ ID NO: 22, and SEQ ID NO: 23. One example of such a single domain antibody, wherein the framework region is that of a human heavy chain variable domain, is a single domain antibody comprising SEQ ID NO: 24 (m536).

In a seventh embodiment, the single domain antibody comprises as the CDRs SEQ ID NO: 25, SEQ ID NO: 26, and SEQ ID NO: 27. One example of such a single domain antibody, wherein the framework region is that of a human heavy chain variable domain, is a single domain antibody comprising SEQ ID NO: 28 (m537).

The dAb can be fused to another polypeptide or other moiety to provide fusion protein or conjugate comprising the dAb. For example, the dAb can be polymerized (fused) to one or more additional antibodies, antibody fragments (e.g., Fab, single chain, ScFv, etc.), or dAbs to provide a multivalent antibody construct. The one or more additional antibodies can be the same or different, i.e., target the same or different antigen. For instance, two or more dAbs that bind to a member of the IGF pathway can be fused together, or a dAb to a member of the IGF pathway can be fused to a dAb to a different antigen that may be another therapeutic target or a molecule that performs some other function, such as cell targeting or enhanced stability (e.g., a dAb to serum albumin). Alternatively, or in addition, the dAb can be fused to another immunoglobulin component, such as an Fc domain of a human or non-human antibody (e.g., human IgG1 Fc), or the dAb can be conjugated or fused with a toxin, a cell-targeting moiety, a stabilizing moiety such as polyethylene glycol (PEG) or a molecule (e.g., peptide) that binds serum albumin, or a label or other detectable moiety (e.g., a radiolabel, a fluorophore, a chromophore, an imaging agent, a metal ion, etc.). Such fusion proteins or conjugates can be produced using standard molecular biology techniques.

Preferably, the fusion proteins have molecular weights of more than 60 kDa (the human kidney filtration limit) but less than that of full-length antibodies (e.g., 150 kDa for an IgG1), thereby having a long half-life in circulation while still retaining better penetration into solid tumors that full-length antibodies. Accordingly, the fusion proteins of the invention can have a molecular weight of at least 60 kDa but less than 150 kDa (e.g., 65 kDa, 70 kDa, 75 kDa, 80 kDa, 90 kDa, 95 kDa, 100 kDa, 105 kDa, 110 kDa, 115 kDa, 120 kDa, 125 kDa, 130 kDa, at 135 kDa, 140 kDa, or 145 kDa).

Any single domain antibody of the invention, whether attached to other sequences or not, can also include insertions, deletions, substitutions, or other selected modifications of particular regions or specific amino acids residues, provided the activity of the single domain antibody is not significantly altered or impaired compared to the non-modified single domain antibody. These modifications can provide for some additional property, such as to remove/add amino acids capable of disulfide bonding, to increase its bio-longevity, to alter its secretory characteristics, etc. In any case, the single domain antibody must possess a bioactive property, such as specific binding to its cognate antigen. Functional or active regions of the single domain antibody may be identified and/or improved by mutagenesis of a specific region of the protein, followed by expression and testing of the expressed polypeptide. For example, amino acid sequence variants of antibodies or antibody fragments can be generated and those that display equivalent or improved affinity for antigen can be identified using standard techniques and/or those described herein. Methods for generating amino acid sequence variants are readily apparent to a skilled practitioner in the art and can include site-specific mutagenesis or random mutagenesis (e.g., by PCR) of the nucleic acid encoding the single domain antibody (Zoller, M. J. *Curr. Opin. Biotechnol.* 3: 348-354 (1992)). Both naturally occurring and non-naturally occurring amino acids (e.g., artificially-derivatized amino acids) may be used to generate amino acid sequence variants of the antibodies and antibody fragments of the invention.

Also provided herein is a nucleic acid that encodes a dAb or fusion polypeptide described herein. Nucleic acids include single stranded and double stranded nucleic acids of any type (e.g., DNA, RNA, DNA/RNA hybrid). Such nucleic acids may find use both therapeutically and in methods of producing the dAb.

The nucleic acid encoding the antibody or fusion polypeptide can be part of a vector. Vectors include nucleic acid vectors, such as naked DNA and plasmids, and viral vectors, such as retroviral vectors, parvovirus-based vectors (e.g., adenoviral-based vectors and adeno-associated virus (AAV)-based vectors), lentiviral vectors (e.g., herpes simplex (HSV)-based vectors), poxviral vectors (e.g., vaccinia virus-based vectors and fowlpox virus-based vectors), and hybrid or chimeric viral vectors, such as an adenoviral backbone with lentiviral components (see, e.g., Zheng et al., *Nat. Biotech.*, 18(2): 176-80 (2000); International Patent Application WO 98/22143; International Patent Application WO 98/46778; and International Patent Application WO 00/17376) and an adenoviral backbone with AAV components (see, e.g., Fisher et al., *Hum. Gene Ther.*, 7: 2079-2087 (1996)). Vectors and vector construction are known in the art (see, e.g., Sambrook et al., *Molecular Cloning: A Laboratory Manual,* 2nd edition, Cold Spring Harbor Laboratory, NY (1989); and Ausubel et al., Current Protocols in Molecular Biology, Green Publishing Associates and John Wiley & Sons, New York, N.Y. (1994)).

The vector can comprise any suitable promoter and other regulatory sequences (e.g., transcription and translation initiation and termination codons, which are specific to the type of host) to control the expression of the nucleic acid sequence encoding the polypeptide. The promoter can be a native or nonnative promoter operably linked to the nucleic acid molecule described above. The selection of promoters, including various constitutive and regulatable promoters, is within the skill of an ordinary artisan. Examples of regulatable promoters include inducible, repressible, and tissue-specific promoters. Specific examples include viral promoters, such as adenoviral, vaccinia virus, and AAV promoters. Additionally, combining the nucleic acid described above with a promoter is within the skill in the art.

A cell (e.g., an isolated host cell) comprising the dAb or nucleic acid molecule encoding the dAb, optionally in the form of a vector, also is provided, which may be useful, for example, as a therapeutic agent or for producing a dAb. Any suitable cell can be used, including prokaryotic and eukaryotic cells. Examples include host cells, such as *E. coli* (e.g., *E. coli* Tb-1, TG-1, DH5α, XL-Blue MRF' (Stratagene), SA2821, and Y1090), *Bacillus subtilis, Salmonella typhimurium, Serratia marcescens, Pseudomonas* (e.g., *P. aerugenosa), N. grassa*, insect cells (e.g., Sf9, Ea4), yeast (*S. cerevisiae*) cells, and cells derived from a mammal, including murine and human cell lines. Specific examples of suitable eukaryotic host cells include VERO, HeLa, 3T3, Chinese hamster ovary (CHO) cells, W138 BHK, COS-7, and MDCK cells. Alternatively, cells from a mammal, such as a human, to be treated in accordance with the methods described herein can be used as host cells. Methods of introducing nucleic acids and vectors into isolated host cells and the culture and selection of transformed host cells in vitro are known in the art and include the use of calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation (see, e.g., Sambrook et al., *Molecular Biology: A Laboratory Manual*, Cold Spring Harbor Laboratory, NY (1989); Davis et al., *Basic Methods in Molecular Biology* (1986); and Neumann et al., *EMBO J.* 1: 841 (1982)). Desirably, the cell comprising the vector or nucleic acid molecule expresses the nucleic acid sequence, such that the nucleic acid sequence is transcribed and translated efficiently by the cell.

The dAbs described herein, as well as any conjugates or fusion proteins, can be produced by a method comprising (a) transforming a cell with a nucleic acid encoding the antibody; (b) culturing the cell in culture medium under conditions sufficient to express the antibody; and (c) harvesting the antibody from the cell or culture medium. The inventive dAbs can be expressed in prokaryotic cells (e.g., bacteria) or eukaryotic cells (e.g., yeast, insect, or mammalian cells), and subsequently harvested and purified, as necessary, using well known methods (see, e.g., Sambrook et al. *Molecular Cloning: a Laboratory Manual*, Cold Spring Harbor Laboratory Press (1989); and Ausubel et al., *Current Protocols in Molecular Biology*, John Wiley & Sons, New York, N.Y. (2001), which is updated quarterly). Specific techniques for transforming, culturing, and harvesting the dAb are known in the art. For example, the dAb can be expressed in a bacterial system, such as *E. coli*, or fungal systems, such as yeast (see, e.g., Holt et al., supra). Alternatively, the dAb can be produced in mammalian, avian, or plant systems (see, e.g., Holt et al., supra). If the dAb has poor solubility, the dAb can be expressed in the form of insoluble inclusion bodies and refolded in vitro (see, e.g., Holt et al., supra). Other aspects of the method of preparing a dAb are as described with respect to the dAb and nucleic acid of the invention.

Other techniques for antibody production know in the art also can be used to produce the dAb. Examples of techniques for antibody production include those described by Cole et al. (*Monoclonal Antibodies and Cancer Therapy*, Alan R. Liss, p. 77 (1985)) and by Boerner et al. (*J. Immunol.*, 147(1): 86-95 (1991)). Also, dAbs can be produced using phage display libraries (Hoogenboom et al., *J. Mol. Biol.*, 227: 381 (1991); Marks et al., *J. Mol. Biol.*, 222: 581 (1991); and C. F. Barbas, D. R. Burton, J. K. Scott, G. J. Silverman, *Phage Display: A Laboratory Manual*, Cold Spring Harbor Laboratory Press, Cold Spring Harbor, N.Y. (2001)).

The dAb can be used for any purpose. For example, a dAb comprising (a) SEQ ID NO: 1, SEQ ID NO: 2, and SEQ ID NO: 3; (b) SEQ ID NO: 5, SEQ ID NO: 6, and SEQ ID NO: 7; or (c) SEQ ID NO: 9, SEQ ID NO: 10, and SEQ ID NO: 11 can be used to inhibit the IGF signaling pathway in a cell or in a mammal. Thus, provided herein is a method of inhibiting the IGF signaling pathway in a cell, which may be in a mammal, comprising administering to the cell or mammal the dAb, whereby the IGF signaling pathway is inhibited. The IGF signaling pathway can be inhibited by any mechanism, without limitation. Thus, for example, the method of inhibiting the IGF signaling pathway can comprise inhibiting phosphorylation of the IGF-1 receptor (IGF-1R).

Furthermore, the method of inhibiting the IGF signaling pathway can be used to achieve any end result, such as for the treatment of a disease associated with IGF overexpression. For example, the method of inhibiting the IGF signaling pathway can be performed by administering the dAb, as described above, to a cell in a mammal afflicted with a disease associated with IGF overexpression, such as cancer. Through practice of the method, one or more symptoms of the disease is alleviated and the disease is, thereby, treated. Treatment of cancer, in particular, can comprise alleviation of any one or more symptoms of the cancer, including, without limitation, an inhibition of the growth of cancer cells, a decrease in metastasis, an increase in cancer cell death, and an increase in the survival of the mammal afflicted with the cancer.

Non-limiting examples of specific types of cancers include cancer of the head and neck, eye, skin, mouth, throat, esophagus, chest, bone, lung, colon, sigmoid, rectum, stomach, prostate, breast, ovaries, kidney, liver, pancreas, brain, intestine, heart or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocytic leukemia, acute undifferentiated leukemia, chronic myelocytic leukemia, chronic lymphocytic leukemia, hairy cell leukemia, or multiple myeloma. See, e.g., Harrison's Principles of Internal Medicine, Eugene Braunwald et al., eds., pp. 491 762 (15th ed. 2001). The methods of the invention are believed to be useful for the treatment of sarcomas (e.g., osteosarcoma and rhabdomyosarcoma), breast, prostate, colon, lung, pancreatic, cervical, ovarian, and endometrial cancers, melanoma, neuroblastoma, multiple myeloma, and hepatocellular carcinoma, as well as any other cancer known to be responsive to inhibitors of the IGF signaling pathway.

IGF-1R activity has been linked to other diseases, including benign prostatic hyperplasia (BPH), diarrhea associated with metastatic carcinoid and vasoactive intestinal peptide secreting tumors (e.g., VIPoma or Werner-Morrison syndrome), acromegaly, gigantism, psoriasis, atherosclerosis, spinocerebellar ataxia and smooth muscle restenosis of blood vessels or inappropriate microvascular proliferation, such as that found as a complication of diabetes, especially of the eye. Thus, the methods of the invention are believed to be useful for the treatment of such diseases, as well.

The single domain antibody can be used alone or in combination with other anti-cancer therapies, such as chemotherapy and radiotherapy.

The single domain antibody can be administered to the mammal directly, or by administering to the mammal a nucleic acid molecule encoding the antibody, optionally in a vector, or a cell comprising the nucleic acid. Nucleic acids, vectors, and cells comprising the nucleic acids are as previously described herein. Furthermore, the dAb can be administered alone or as part of a conjugate or fusion molecule, as previously described.

The cell can be any type of cell, as discussed elsewhere herein, especially a cancer cell. When the cell is in a mammal, the mammal can be any suitable mammal, such as a mouse, rat, guinea pig, hamster, rabbit, cat, dog, sheep, cow, horse, pig, or primate. Preferably, the mammal is a human.

The dAb, conjugate, fusion protein, nucleic acid molecule, vector, or cells, can be administered to a mammal alone, or in combination with a carrier (i.e., a pharmaceutically acceptable carrier). By pharmaceutically acceptable is meant a material that is not biologically or otherwise undesirable (i.e., the material can be administered to a mammal, along with the single domain antibody, nucleic acid, vector, or cell, without causing any undesirable biological effects or interacting in a deleterious manner with any of the other components of the pharmaceutical composition in which it is contained). The carrier is selected to minimize any degradation of the agent and to minimize any adverse side effects in the mammal, as would be well-known to one of ordinary skill in the art.

Suitable carriers and their formulations are described in Remington: *The Science and Practice of Pharmacy* (19th ed.) ed. A. R. Gennaro, Mack Publishing Company, Easton, Pa. (1995). Pharmaceutical carriers, include sterile water, saline, Ringer's solution, dextrose solution, and buffered solutions at physiological pH. Typically, an appropriate amount of a pharmaceutically acceptable salt is used in the formulation to render the formulation isotonic. The pH of the solution is preferably from about 5 to about 8 (e.g., about 5.5, about 6, about 6.5, about 7, about 7.5, and ranges thereof). More preferably, the pH is about 7 to about 7.5. Further carriers include sustained-release preparations, such as semipermeable matrices of solid hydrophobic polymers containing the polypeptide, which matrices are in the form of shaped articles (e.g., films, liposomes, or microparticles). It will be apparent to those persons skilled in the art that certain carriers may be more preferable depending upon, for instance, the route of administration and concentration of composition being administered.

Compositions (e.g., pharmaceutical compositions) comprising the single domain antibody, nucleic acid molecule, vector, or cell can include carriers, thickeners, diluents, buffers, preservatives, surface agents, and the like. The compositions also can include one or more active agents, such as an antimicrobial agent, an anti-inflammatory agent, an anesthetic, an anti-viral agent, or a cytotoxic agent (e.g., a chemotherapeutic agent, a small drug, a prodrug, a taxoid, or a toxin).

The composition (e.g., pharmaceutical composition) comprising the single domain antibody, nucleic acid molecule, vector, or cell can be administered (e.g., to the mammal, a cell, a tissue, or a tumor) in any suitable manner depending on whether local or systemic treatment is desired, and on the area to be treated. Administration can be topically (including ophthalmically, vaginally, rectally, intranasally, transdermally, and the like), orally, by inhalation, or parenterally (including by intravenous drip or subcutaneous, intracavity, intraperitoneal, intradermal, or intramuscular injection). Topical intranasal administration refers to the delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. Alternatively, administration can be intratumoral. Local or intravenous injection is preferred.

If the composition is to be administered parenterally, the administration is generally by injection. Injectables can be prepared in conventional forms, either as liquid solutions or suspensions, solid forms suitable for solution of suspension in liquid prior to injection, or as emulsions. Additionally, parental administration can involve the preparation of a slow-release or sustained-release system, such that a constant dosage is maintained (see, e.g., U.S. Pat. No. 3,610,795). Preparations for parenteral administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, anti-oxidants, chelating agents, and inert gases and the like.

Formulations for topical administration may include ointments, lotions, creams, gels, drops, suppositories, sprays, liquids, and powders. Conventional pharmaceutical carriers; aqueous, powder, or oily bases; thickeners; and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable.

Some of the compositions can potentially be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines.

Additionally, probiotic therapies are envisioned by the present invention. Viable host cells containing the nucleic acid molecule or vector of the invention and expressing the single domain antibody can be used directly as the delivery vehicle to the desired site(s) in vivo. Preferred host cells for the delivery of the single domain antibody directly to desired site(s), such as, for example, to a selected body cavity, can comprise bacteria. More specifically, such host cells can comprise suitably engineered strain(s) of lactobacilli, enterococci, or other common bacteria, such as E. coli, normal strains of which are known to commonly populate body cavities. More specifically yet, such host cells can comprise one or more selected nonpathogenic strains of lactobacilli, such as those described by Andreu et al. (J. Infect. Dis., 171(5): 1237-43 (1995)), especially those having high adherence properties to epithelial cells (e.g., vaginal epithelial cells) and suitably transformed using the nucleic acid molecule or vector of the invention.

The single domain antibody, conjugate, fusion protein, nucleic acid molecule, vector, or cell can be administered with a pharmaceutically acceptable carrier and can be delivered to the mammal in vivo and/or ex vivo by a variety of mechanisms well-known in the art. If ex vivo methods are employed, cells or tissues can be removed and maintained outside the body according to standard protocols known in the art. The compositions can be introduced into the cells or tissue via any gene transfer mechanism, such as calcium phosphate mediated gene delivery, electroporation, microinjection, or proteoliposomes. The transduced cells then can be infused (e.g., with a pharmaceutically acceptable carrier) or homotopically transplanted back into the mammal per standard methods for the cell or tissue type. Standard methods are known for transplantation or infusion of various cells into a mammal.

The exact amount of the single domain antibody, conjugate, fusion protein, nucleic acid molecule, vector, cell, or compositions thereof required to elicit the desired effect will vary from mammal to mammal, depending on the species, age, gender, weight, and general condition of the mammal, the particular single domain antibody, nucleic acid molecule, vector, or cell used, the route of administration, and whether other drugs are included in the regimen. Thus, it is not possible to specify an exact amount for every composition. However, an appropriate amount can be determined by one of ordinary skill in the art using only routine experimentation given the teachings herein. The dosage ranges for the administration of the compositions are those large enough to produce the desired effect; however, the dosage should not be so large as to cause adverse side effects, such as unwanted cross-reactions, anaphylactic reactions, and the like. Dosage can vary, and can be administered in one or more (e.g., two or more, three or more, four or more, or five or more) doses daily, for one or more days. Guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the single domain antibody used alone might range from about 1 µg/kg to up to 100 mg/kg of body weight or more per day, depending on the factors mentioned above.

The invention also includes kits comprising the single domain antibody, nucleic acid molecule, vector, cell, or compositions thereof. The kit can include a separate container containing a suitable carrier, diluent, or excipient. The kit also can include an adjuvant, cytokine, active agent, immunoassay reagents, PCR reagents, radiolabels, and the like. Additionally, the kit can include instructions for mixing or combining ingredients and/or administration.

The single domain antibody can be used to detect the presence of IGF-2 or IGF-1R in a sample. Such a method can comprise contacting a sample with the single domain antibody, wherein binding of the single domain antibody to IGF-2 or IGF-1R indicates the presence of IGF-2 or IGF-1R in the sample. Any suitable sample can be used, such as blood, serum, cells, or tissue isolated from a mammal (e.g., a human). Furthermore, the sample can be contacted with the single domain antibody by any suitable method. For instance, the antibody can simply be combined with the sample, or the antibody can be immobilized on a substrate and the sample applied to the substrate. Thereafter, the substrate can be washed and examined for the presence of bound antigen. Other common techniques also can be used. Similarly, the binding of the antibody to the antigen can be detected by routine techniques, including the use of labels and/or probes to detect bound antigen or antibody-antigen complexes. All other aspects of the method are as previously described with respect to the single domain antibody of the invention.

The following examples further illustrate the invention but, of course, should not be construed as in any way limiting its scope.

EXAMPLE 1

This example demonstrates the design and construction of a large phage-displayed domain antibody (dAb) library.

The m81 library previously was constructed based on highly stable, soluble VH scaffold, m0, by grafting in vivo formed CDR2 (H2) and CDR3 (H3), and randomizing four putative solvent accessible residues in the CDR1 (H1) of m0 to A, D, S, and Y, which are residues most widely used in human antibodies (see, e.g., Chen et al., Methods Mol. Biol., 525: 81-99 (2009); and Chen et al., J. Mol. Biol., 382: 779-789 (2008)). In order to increase diversity and minimize immunogenicity, a human antibody light chain CDR3 (L3) repertoire was grafted into the H1 of the m81 library, which resulted in the generation of a new library (designated m91), which combined the most diversified CDRs of an antibody (L3, H2, and H3) in the same scaffold.

To efficiently amplify highly diverse L3 repertoires, primers based on human germline VL sequences were designed. The sense primers targeted the last three residues of the light chain FR3 (LFR3) that are highly conserved among different families of kappa (KL) and lambda (LL) light chains. The antisense primers targeted the first three residues of the J gene product. Thus, the PCR products contained L3 plus an additional three residues from LFR3.

Since the amplification of L3 was inefficient when cDNA or plasmid DNA was used directly as a template, full-length KL and LL first were amplified under standard conditions (using primers described in Zhu et al., Methods Mol. Biol., 525: 129-142 (2009)), gel purified, and then used as templates for L3 amplification. Because the last residue of LFR3 (position 104, IMGT annotation) is cysteine in almost all germline sequences (which could affect protein folding leading to a low yield of properly folded antibodies), the cysteine was mutated to serine or glycine following the amplification and pooling of the kappa (KL3) and lambda (LL3) L3 repertoires. The two other residues of LFR3

(positions 102 and 103, IMGT annotation) are most frequently are tyrosine, which is highly hydrophobic. To reduce the possibility of antibody aggregation, the tyrosine at position 102 (IMGT annotation) was mutated to aspartic acid, asparagine, or histidine. Low annealing temperature (40° C.) was used from the PCR mutagenesis to allow for efficient secondary amplification of the L3 fragments containing the desired mutation.

For assembly of full-length VHs, human H2 and H3 repertoires and the FR2, FR3, and FR4 of m0 were amplified as a whole from the m81 library. The FR1 of m0 also was PCR-amplified from the m81 plasmid DNA and joined to the L2 repertoire by overlapping PCR. The entire chimeric VHs were assembled by further joining the L3 repertoire to the H2 and H3 repertoires. The products were cloned into phagemid pComb3X and a large (about $10^{10}$) library (designated m91) was obtained by performing 100 electroporations.

To estimate the degree of diversity of the m91 library, 126 randomly selected dAb clones were analyzed for their gene usage, somatic mutations, CDR length, and how different CDRs are combined. There were no identical L3 and H3 sequences found. H2s were less diverse with three groups (with 19, 4, and 3 members, respectively) of sequences containing identical H2s from VH families 7, 4, and 4, respectively. Of the 126 L3 sequences, 88 were derived from all families of KL except family 7. About 75% of the 88 sequences were from family 1 of KL. The sequences varied in length from 10 to 14 residues and more than 90% were 10 residues in length.

The remaining 38 L3 sequences were from only 2 of 11 LL families. More than 80% of the 38 sequences were from family 1. The L3 sequences varied in length from 9 to 12 residues. Most of the L3 sequences (82.5%) were mutated in their V genes compared to the closest corresponding germline genes. 57% contained two or more mutations in their amino acid sequences.

The distribution and somatic mutations of H2s in m91 were consistent with those in m81 except that in m91, H2 gene usage was biased slightly toward VH1 and VH7, while VH2- and VH6-derived sequences were absent.

The H3 lengths of dAbs from m91 ranged from 5 to 23 residues. The distribution was in agreement with the reported frequency in m81, but there was an increased number of H3s with lengths shorter than 9 residues and longer than 18 residues.

In order to determine the combinatorial diversity of the library, the pairing between the L3 origin, H2 origin, and H3 length was plotted. Regardless of the preferential amplification of gene fragments from certain families, the CDRs were paired randomly. These results indicate a high degree of diversity in the m91 library.

In order to analyze the dAbs from the m91 library for certain biophysical properties such as oligomerization, aggregation, and degradation, four dAbs were randomly selected and more extensively characterized. After purification on Ni-nitrilotriacetic acid resin, the four dAbs were dialyzed against phosphate buffered saline (PBS, pH 7.4, concentrated, and subjected to long-term storage at 4° C. No precipitation was observed with these four dAb solutions immediately after purification and concentration. After storage for about one year, one dAb showed obvious precipitation (pellet) after centrifugation. Supernatent fractions were collected and measure for optical density at 280 nm. No significant degradation was observed. When run on reducing SDS-PAGE, the four dAbs had apparent molecular weights of about 16 kDa, which is similar to the calculated molecular weights of 15-17 kDa. Two of the dAbs ran faster than the others on a native PAGE with an apparent molecular weight that is much lower than their calculated molecule weight, suggesting that these dAbs may fold more tightly.

The oligomerization of these dAbs was measured by size-exclusion chromatography on a Superdex-75 column. The dAbs were eluted as mono-disperse symmetric peaks, indicating that the dAbs did not stick to the column matrix. Only one of the dAbs eluted at the expected size of a monomer, which variations in the apparent molecular weight were observed with the other dAbs, which eluted more rapidly or slowly Interestingly, the elution of two of these dAbs, as well as m36, which is a well-characterized monomeric dAb (with a calculated molecular weight of about 15 kDa) from the m81 library, was further delayed in the presence of 300 nM NaCl, suggesting an increased hydrophobicity of these antibodies. These results suggest that randomly selected dAbs from the m91 library generally are stable against aggregation, but may exhibit variations in their apparent molecular weights.

It was observed that staphylococcal protein A (SPA) binds to the VH domain containing the VH3 gene products. Therefore, the library was panned against SPA in order to investigate possible conformational changes in the scaffold caused by the grafted L3s. Forty-six and 43 clones were picked randomly from the third and fourth round of panning, respectively, sequenced, and analyzed for L3 and H2 gene usage and H3 length. There was an increased number (70%, 89%, and 91% for the original library, the third round, or the fourth round, respectively) of antibodies with KL3s. The frequencies of V and J gene usages in the KL3s selected after panning were comparable with those for the original library. The frequency of antibodies composed of VH3-derived H2 was increased dramatically (4- to 5-fold) and their H3s were diverse with lengths ranging from 7 to 20 residues. These results suggest that the VH3-based scaffold used in the library, m0, preserves its conformational integrity after grafting of KL3s from almost all families, as evaluated by SPA binding activity.

EXAMPLE 2

This example describes the isolation of several fully humanized dAbs against human IGF-1R or IGF ligand 2 (IGF-2).

The libraries described in Example 1 (m81 and m91) were screened for high affinity binding to IGF-1R or IGF-2. Several fully humanized domain antibodies were isolated. The domain antibodies were one magnitude smaller than regular IgG and were fully human. As a result, the antibodies have better solid tumor penetration capability compared with regular IgG and minimal toxic effects and immunogenicity.

Two antibodies designated m632 (corresponding to SEQ ID NO: 4) and m636 (corresponding to SEQ ID NOs: 8) were selected from library m91. m632 and m636 bound with high affinity to IGF-2 as determined by ELISA. m636 was cross-reactive for both IGF-1 and IGF-2.

Five antibodies designated m546 (corresponding to SEQ ID NO: 12), m534 (corresponding to SEQ ID NO: 16), m535 (corresponding to SEQ ID NO: 20), m536 (corresponding to SEQ ID NO: 24), and m537 (corresponding to SEQ ID NO: 28) bound with high affinity to IGF-1R as determined by ELISA. m534 and m535 were selected from library m81. m536, m537, and m546 were selected from library m91. The sequences of identified antibodies, as well as the respective CDRs, are set forth in Table 1.

TABLE 1

Sequences of dAbs

| Ab | SEQUENCE | SEQ ID NO |
|---|---|---|
| m632 | QVQLVQSGGGLVQPGGSLRLSCAASDYS<u>QQYKTYPLTF</u>MSWVRQAPGQRLEWVAG<u>ISGSGGTT</u>VYADSVKGRFTISRDNSKNTLYLQMNTLRAEDTAMYYC<u>ARVASRDYFDY</u>WGQGTLVTVSS | 4 |
| | CDR1 <u>QQYKTYPLTF</u> | 1 |
| | CDR2 <u>ISGSGGTT</u> | 2 |
| | CDR3 <u>ARVASRDYFDY</u> | 3 |
| m636 | QVQLVQSGGGLVQPGGSLRLSCAASYYS<u>LQHDNFPYTF</u>MSWVRQAPGQRLEWVSG<u>ISGSGGST</u>YYADSVKGRFTISRDNSKNTLYLQMNTLRAEDTAMYYC<u>ARIRWLQDLDY</u>WGQGTLVTVSS | 8 |
| | CDR1 <u>LQHDNFPYTF</u> | 5 |
| | CDR2 <u>ISGSGGST</u> | 6 |
| | CDR3 <u>ARIRWLQDLDY</u> | 7 |
| m546 | QVQLVQSGGGLVQPGGSLRLSCAASYYS<u>QQYNSYPITF</u>MSWVRQAPGQRLEWVAS<u>INQDGSQI</u>DYAGSVKGRFTISRDNSKNTLYLQMNTLRAEDTATYYC<u>AVDLRSGARNFQH</u>WGQGTLVTVSS | 12 |
| | CDR1 <u>QQYNSYPITF</u> | 9 |
| | CDR2 <u>INQDGSQI</u> | 10 |
| | CDR3 <u>AVDLRSGARNFQH</u> | 11 |
| m534 | QVQLVQSGGGLVQPGGSLRLSCAAS<u>DFYFYDYE</u>MSWVRQAPGKGLEWIGS<u>ISHGGI</u>THYTYSLKSRVTISRDNSKNTLYLQMNTLRAEDTAMYYC<u>ARDYGYAFDI</u>WGQWTTGTVSS | 16 |
| | CDR1 <u>DFYFYDYE</u> | 13 |
| | CDR2 <u>ISHGGIT</u> | 14 |
| | CDR3 <u>ARDYGYAFDI</u> | 15 |
| m535 | QVQLVQSGGGLVQPGGSLRLSCAAS<u>SFSFSDYE</u>MSWVRQAPGKGLEWVAH<u>INSDGVI</u>QYADSVKGRFTISRDNSKNTLYLQMNTLRAEDTATYYC<u>VRVAVPGKRYFQY</u>WGQGTTVTVSS | 20 |
| | CDR1 <u>SFSFSDYE</u> | 17 |
| | CDR2 <u>INSDGVI</u> | 18 |
| | CDR3 <u>VRVAVPGKRYFQY</u> | 19 |
| m536 | QVQLVQSGGGLVQPGGSLRLSCAASYYG<u>QSFDSDSVVF</u>MSWVRQAPGKGLEWISS<u>MSNTGTYI</u>DYADSVKGRFTISRDNSKNTLYLQMNTLRAEDTATYYC<u>VKEWDRGLRRLQH</u>WGQGTVVTVSS | 24 |
| | CDR1 <u>QSFDSDSVVF</u> | 21 |
| | CDR2 <u>MSNTGTYI</u> | 22 |
| | CDR3 <u>VKEWDRGLRRLQH</u> | 23 |
| m537 | QVQLVQSGGGLVQPGGSLRLSCAASNYS<u>QQTYSAPITF</u>MSWVRQAPGQGLEWVSS<u>TSWNGGTT</u>DYADSVKGRFTISRDNSKNTLYLQMNTLRAEDTAMYYC<u>VTDTSGWRYFQD</u>WGQGTLVTVSS | 28 |
| | CDR1 <u>QQTYSAPITF</u> | 25 |
| | CDR2 <u>TSWNGGTT</u> | 26 |
| | CDR3 <u>VTDTSGWRYFQD</u> | 27 |

EXAMPLE 3

This example demonstrates the characterization of the dAbs identified in Example 2.

dAbs m632, m636, and m546 were shown to inhibit phosphorylation of IGF-1R, the first step in the IGF mediated pathway, which indicates their utility in human IGF related cancer therapy. In a first experiment, overnight-starved MCF-7 cells (human breast cancer cell line) were treated with 10 nM IGF-2 and various concentrations of IGF-2 dAb (m636) or dAb-Fc fusion protein (m632Fc) ranging from 0.4 to 400 nM. In a second experiment, the overnight-starved MCF-7 cells were treated with 2 nM IGF-1 and various concentrations of IGF-1R dAb-Fc fusion protein (m546Fc) ranging from 2-200 nM.

The IGF-1R beta subunit was immunoprecipitated, and tyrosine-phosphorylated IGF-1R (Pi IGF-1R) was detected with Western blot. The same membrane was re-probed with IGF-1R Ab to demonstrate the total amount of IGF-1R per lane of the Western blot. These experiments demonstrated that m636 and m632Fc significantly inhibited IGF-2-induced phosphorylation of IGF-1R in MCF-7 cells, while m546Fc significantly inhibited IGF-1-induced phosphorylation of IGF-1R.

In contrast, dAbs m534, m535, m536, and m537 did not significantly inhibit phosphorylation of IGF-1R. In a first experiment, overnight starved MCF-7 cells were treated with 2 nM IGF-1 and various concentrations of IGF-1R dAbs (m534, m535, m536, or m537) ranging from 2 to 200 nM. In a second experiment, overnight starved MCF-7 cells were treated with 2 nM IGF-1 and various concentrations of m535Fc fusion protein.

The IGF-1R beta subunit was immunoprecipitated, and tyrosine-phosphorylated IGF-1R (Pi IGF-1R) was detected with Western blot. The same membrane was re-probed with IGF-1R Ab to demonstrate the total amount of IGF-1R per lane of the Western blot. These experiments demonstrated that m534, m535, m536, m537, and m535Fc did not significantly inhibit IGF-1-induced phosphorylation of IGF-1R on MCF-7 cells.

Although dAbs m534, m535, m536, and m537 did not inhibit the IGF signaling pathway, they showed high affinity binding to IGF-1R (as described in Example 2). Thus, dAbs m534, m535, m536, and m537 can be used as diagnostic or research agents, such as drug carriers, since the antibodies did not interrupt the IGF signaling pathway's normal biological functions and, thus, would cause no side-effects to the human body.

EXAMPLE 4

This example demonstrates the treatment of cancer using the inventive antibodies.

A mouse model of neuroblastoma is prepared using standard methods. The IGF-IR dAb designated m546 is administered to the mouse model, and the effect of the dAb upon the growth of the neuroblastoma cells is observed.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A single domain antibody that binds insulin-like growth factor 2 (IGF-2), comprising a heavy chain variable domain having a complementarity determining region (CDR) 1 comprising the amino acid sequence of SEQ ID NO: 5, a CDR2 comprising the amino acid sequence of SEQ ID NO: 6, and a CDR3 comprising the amino acid sequence of SEQ ID NO: 7.

2. The single domain antibody of claim 1, comprising the amino acid sequence of SEQ ID NO: 8.

3. A fusion protein or conjugate comprising the single domain antibody of claim 1, and a cytotoxic agent, cell targeting motif, a second single domain antibody, or a label.

4. A composition comprising the antibody of claim 1 and a pharmaceutically acceptable carrier.

5. A method for inhibiting an insulin-like growth factor (IGF) mediated signaling pathway in a cell, comprising administering to the cell the single domain antibody of claim 1.

6. A method for inhibiting the phosphorylation of IGF-1R in a cell, comprising administering to the cell the single domain antibody of claim 1.

7. A method of detecting the presence of IGF-2 in a sample, comprising contacting the sample with the single domain antibody of claim 1, wherein binding of the single domain antibody to IGF-2 indicates the presence of IGF-2 in the sample.

8. A kit for detecting the presence of IGF-2 in a sample, comprising the single domain antibody of claim 1 and a separate container containing a suitable carrier, diluent, or excipient.

* * * * *